United States Patent
Kusakabe et al.

[11] Patent Number: 5,980,248
[45] Date of Patent: *Nov. 9, 1999

[54] MOTOR CONTROLLER FOR A DENTAL HANDPIECE

[75] Inventors: Hiroaki Kusakabe; Kazunari Matoba; Masanobu Yoshida, all of Kyoto, Japan

[73] Assignee: Kabushiki Kaisha Morita Seisakusho, Kyoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/690,236

[22] Filed: Jul. 19, 1996

[30] Foreign Application Priority Data

Jul. 28, 1995 [JP] Japan ................................. 7-212830

[51] Int. Cl.⁶ ........................................................ A61C 1/06
[52] U.S. Cl. ............................................ 433/27; 433/131
[58] Field of Search ............................... 433/27, 76, 102, 433/103, 106, 114, 131; 408/8, 9

[56] References Cited

U.S. PATENT DOCUMENTS

| | | | |
|---|---|---|---|
| 4,243,388 | 1/1981 | Arai | 433/27 |
| 4,723,911 | 2/1988 | Kurtz | 433/27 |
| 4,822,215 | 4/1989 | Alexander | 408/9 |
| 4,934,934 | 6/1990 | Arpaio, Jr. et al. | 433/102 |
| 4,955,810 | 9/1990 | Levy | 433/114 |
| 5,017,134 | 5/1991 | Saito et al. | 433/72 |
| 5,038,084 | 8/1991 | Wing | 318/268 |
| 5,116,168 | 5/1992 | Aihara | 408/9 |
| 5,538,423 | 7/1996 | Coss et al. | 433/27 |
| 5,542,304 | 8/1996 | Sasada et al. | 73/862.333 |
| 5,543,695 | 8/1996 | Culp et al. | 318/432 |

FOREIGN PATENT DOCUMENTS

| | | | |
|---|---|---|---|
| 392518 | 10/1990 | European Pat. Off. | 433/102 |
| 3447639 | 7/1986 | Germany | 433/27 |
| 5064643 | 3/1993 | Japan | 433/102 |

*Primary Examiner*—Ralph A. Lewis
*Attorney, Agent, or Firm*—Koda & Androlia

[57] ABSTRACT

A motor controller for a dental handpiece comprising a torque detection means for detecting the load torque applied to a cutting tool, and a control means for stopping a cutting tool drive motor, reducing the rotation speed of the motor or temporarily reversing the motor when the detected load torque has reached a preset reference torque. With this controller, a cutting tool such as a relatively slender file for root canal formation can be prevented from breaking. In addition, the operability of the handpiece can be improved, and operation such as root canal formation can be conducted easily.

26 Claims, 8 Drawing Sheets

MOTOR CONTROLLER FOR A DENTAL HANDPIECE

BACKGROUND OF THE INVENTION

1. Field of the Invention

The present invention relates to a controller for a cutting tool drive motor of a dental handpiece which is used to cut teeth and to form root canals by driving a cutting tool installed at the tip of the handpiece.

2. Description of the Prior Art

Since a motor for dental treatment is mainly used to drive a cutting tool for cutting teeth or the like, a drive method has been adopted, wherein the rotation speed of the motor is not reduced but maintained at a preset speed even when the motor undergoes a large load. As a general example of such a method, feedback control has been known, wherein the rotation speed of the motor detected by a sensor installed in a handpiece is compared with a preset speed, and the voltage for driving the motor is controlled so as to eliminate the difference between the two speeds, thereby maintaining the rotation speed constant. The output of the motor is adjusted by changing the preset speed.

However, as the cutting tool becomes slender, it is apt to break easily, since the rotation speed is maintained constant regardless of the load applied to the cutting tool. Therefore, a relatively slender cutting tool, for example a file for forming root canals, more particularly a Ni-Ti file specified to have the maximum rotation speed of 300 rpm, is apt to break very easily, thereby causing the problem of making dental operation difficult.

SUMMARY OF THE INVENTION

Accordingly, a first object of the present invention is to prevent the cutting tool for a dental handpiece from breaking, a second object of the present invention is to improve the operability of the handpiece, and a third object of the present invention is to facilitate dental operation, such as root canal formation.

To achieve the above-mentioned objects, the motor controller for a dental handpiece in accordance with the present invention comprises a detection means for detecting a load torque applied to the cutting tool, and a control means for stopping a cutting tool drive motor or for reducing the rotation speed thereof when the detected load torque has reached a preset reference torque. With this kind of configuration, cutting is stopped substantially when the load torque has reached the reference torque. Therefore, even when the cutting tool is relatively slender and apt to break easily, particularly when a file for forming root canals is used, it is possible to prevent the tool from breaking by properly setting the reference torque.

Instead of stopping the cutting tool drive motor or reducing the rotation speed of the motor as described above when the load torque has reached the reference torque, it may be possible to reverse the motor. This configuration not only stops cutting but also prevents the cutting tool from remaining cutting into a root canal during root canal formation operation, whereby the operation can be performed efficiently.

In addition to the above-mentioned configuration, a root canal length measurement means, which is also used as an electrode for measuring the cutting tool, is provided to detect the position of the cutting tool. With this configuration, when the load torque has reached the reference torque, or when the cutting tool has reached a preset reference position, it may be possible to stop the cutting tool drive motor, reduce the rotation speed of the motor, or reverse the motor. This configuration prevents the cutting tool from breaking and cutting into a root canal, and also prevents the cutting tool from enlarging or penetrating root apexes, whereby the operability and practical utility of a root canal treatment apparatus can be improved significantly.

Furthermore, each time the load torque has reached the reference torque or each time the cutting tool has reached the reference position, it may be possible to temporarily reverse the cutting tool drive motor and then rotate the motor forward again so that cutting can be resumed by repeating the reverse and forward rotations. This configuration enables efficient operation. The forward rotation to be resumed after the reverse rotation in the above-mentioned case is attained by forward motor rotation control which is performed immediately after the detected load torque has become smaller than the reference torque or immediately after the detected position of the cutting tool is shallower than the reference position. In addition, control, wherein the operation shifting to forward rotation has a hysteresis characteristic, can also be used. In the latter case, the forward and reverse rotations are not repeated frequently, thereby stabilizing the operation, improving the operability, and not adversely affecting the service life of the apparatus.

The basic configurations of the controller have been described above. More specific configurations will be clarified by the explanations for following embodiments.

DETAILED DESCRIPTION OF THE PREFERRED EMBODIMENTS

An embodiment is described below, wherein a controller in accordance with the present invention is provided with a torque detection means and a position detection means comprising a root canal length measurement circuit. In the following explanations, the control wherein motor stop or rotation speed reduction is performed when the above-mentioned load torque has reached the reference torque is referred to as "auto-stop control depending on torque," and the control wherein temporary motor reverse rotation is performed when the load torque has reached the reference torque is referred to as "auto-reverse control." In addition, the control wherein motor stop, rotation speed reduction or reverse rotation is performed when the cutting tool has reached the reference position is referred to as "auto-stop control depending on tool position," and this control includes motor reverse rotation.

Figure 1:
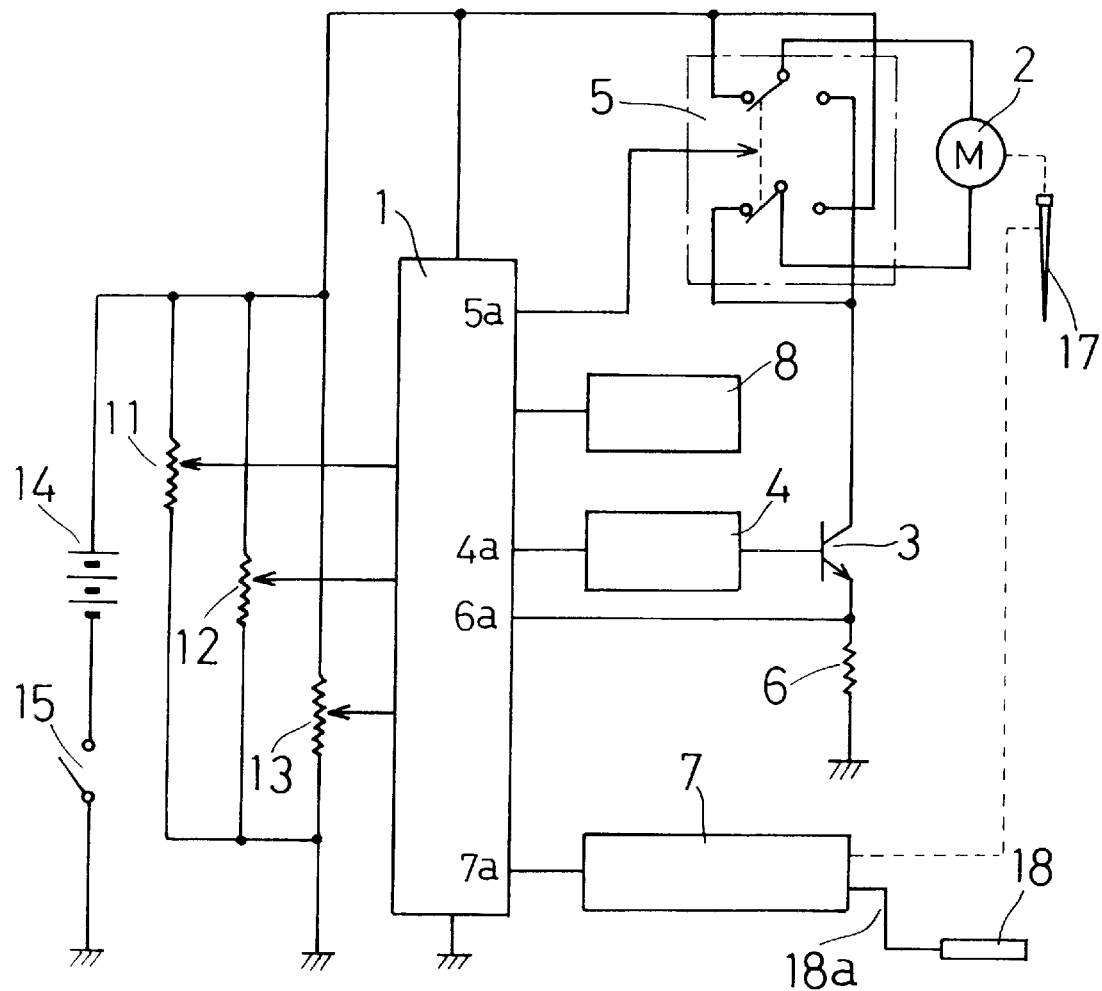
FIG. 1 is a circuit diagram of a motor controller in accordance with an embodiment of the present invention.

Referring to FIG. 1, numeral 1 designates a CPU, numeral 2 designates a cutting tool drive motor, numeral 3 designates a transistor switch, numeral 4 designates a driver circuit, numeral 5 designates a rotation direction selection switch, numeral 6 designates a load torque detection resistor, numeral 7 designates a root canal length measurement circuit, numeral 8 designates a display device, numeral 11 designates a variable resistor for setting the reference torque, numeral 12 designates a variable resistor for setting duty ratio, numeral 13 designates a variable resistor for setting the reference position, numeral 14 designates a battery, and numeral 15 designates a main switch. These are connected to the CPU 1 as shown in the figure. Numeral 17 designates a cutting tool connected to the motor 2 via an appropriate gear mechanism or the like, and numeral 18 designates a grounding electrode for root canal length measurement.

Figure 2A:
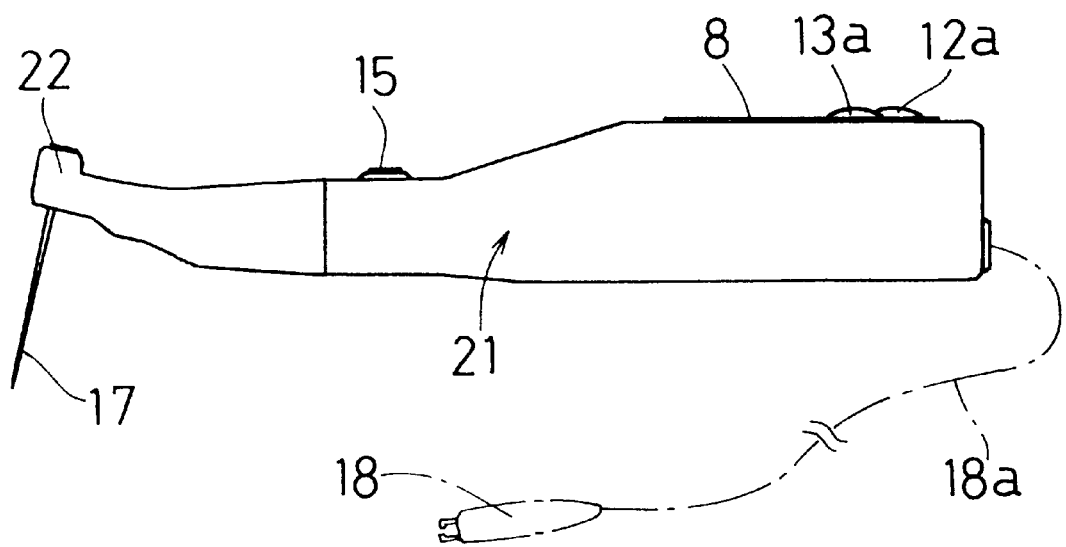
FIG. 2A is a side view showing a handpiece provided with the controller in accordance with the embodiment.
Figure 2B:
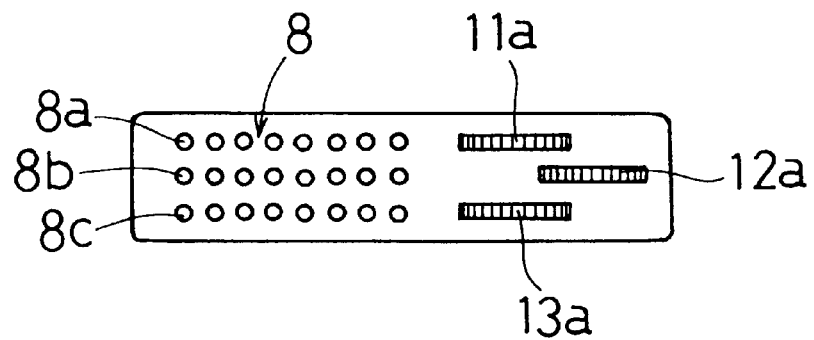
FIG. 2B is a plan view showing the display device of the handpiece.

FIG. 2A is an external view of a cordless-type handpiece 21 provided with members constituting the circuit shown in FIG. 1. In this embodiment, a file for root canal formation is installed at the tip of the head 22 of the handpiece 21 as the cutting tool 17 (hereinafter referred to as the file 17). Since the file 17 is also used as a root canal length measurement terminal, the file 17 is electrically connected to the measurement terminal of the root canal length measurement circuit 7 via the conductive members inside the handpiece 21. The grounding electrode 18 is connected to the grounding terminal of the root canal length measurement circuit 7 via a lead wire 18a. Referring to FIG. 2B, the display device 8 is provided with three display portions: a duty ratio display portion 8a, a reference torque display portion 8b and a reference position display portion 8c, each portion comprising a row of plural LEDs. The display portions 8a, 8b and 8c are provided with rotation knobs 11a, 12a and 13a corresponding to variable resistors 11, 12 and 13, respectively.

In the above-mentioned configuration of the handpiece 21, the file having a predetermined specifications is selected and installed to the head 22, and the grounding electrode 18 is connected as necessary to the tissue in the mouth of a patient. Operation is started by turning on the main switch 15.

The handpiece 21 is not limited to such a cordless type as described above. It is needless to say that the present invention is applicable to motor control for a cord-type handpiece connected to the main unit of a stationary controller via a cord. In the case of the cord-type handpiece, the display device 8 can be divided into two display devices: a display device provided on the handpiece as described above and a large display device comprising LCDs or the like provided on the main unit of the controller. Furthermore, part of the circuit shown in FIG. 1 can also be provided in the main unit of the controller.

Figure 3:
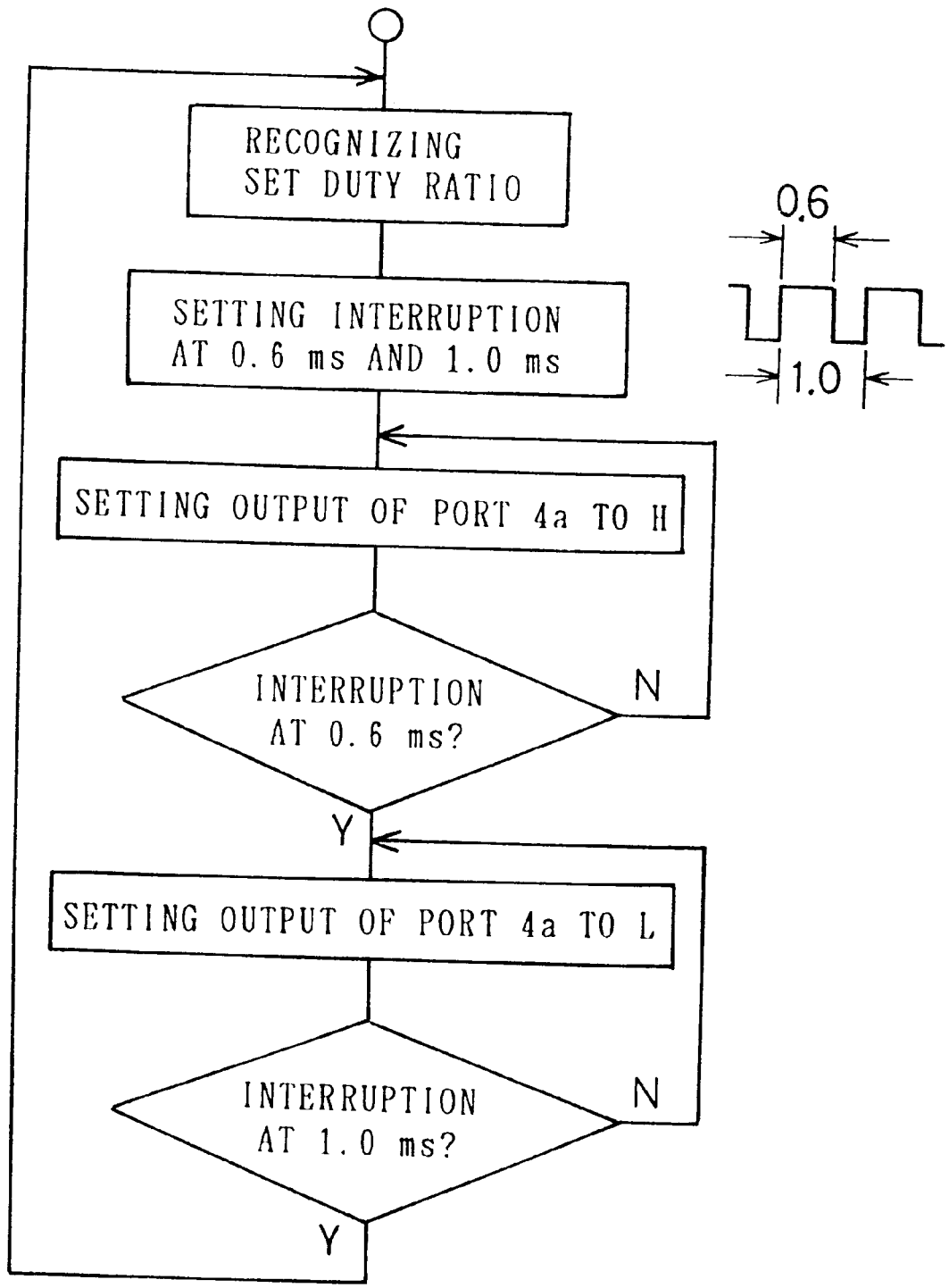
FIG. 3 is a flowchart showing the procedure for the duty ratio control of the controller.

Driven by the control signal delivered from the port 4a of the CPU 1, the transistor driver circuit 4 turns on and off the transistor switch 3 to drive the motor 2. The motor 2 rotates in the forward or reverse direction depending on the state of the rotation direction selection switch 5. In this embodiment, the control signal of the CPU 1 has a pulse waveform repeatedly generated in a constant period. The width, namely the duty ration of the pulse, is adjusted by the variable resistor 12 for setting the duty ratio. The motor 2 is driven by the output corresponding to the duty ratio. The flowchart in FIG. 3 shows the procedure for the control at the CPU 1, wherein a period of 1 ms and a duty ratio of 60% are taken as examples.

As described above, feedback control for keeping the rotation speed constant is not used in the present invention. Therefore, as the load torque applied to the file 17 increases, the rotation speed reduces as an output characteristic of the motor 2. In addition, as the duty ratio is higher, the output torque becomes larger. Accordingly, when the load torque increases, the rotation speed reduction ratio becomes larger, as the duty ratio is lower. However, the maximum value of the pulse voltage applied to the motor 2 remains unchanged even when the duty ratio is changed. The present duty ratio is indicated by the duty ratio display portion 8a.

Figure 4:
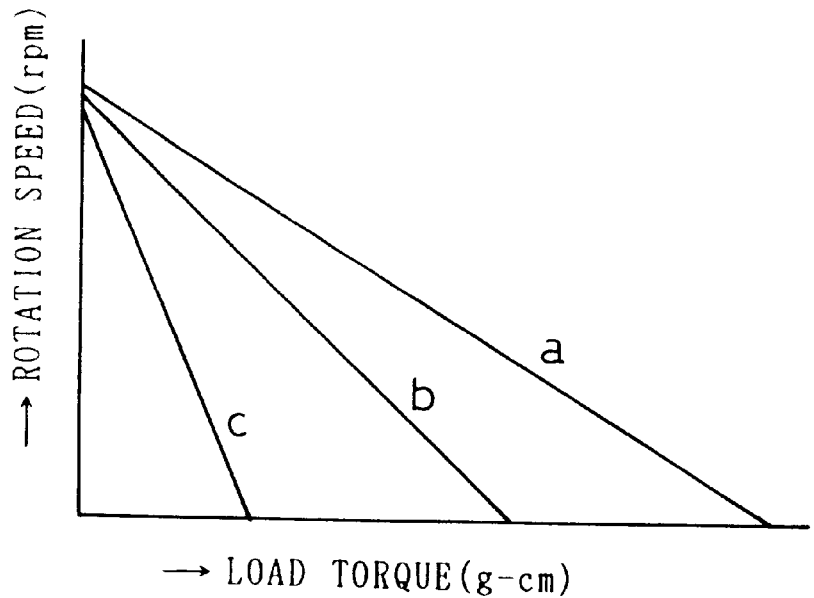
FIG. 4 is a graph showing a motor output characteristic of the controller.

Consequently, the output characteristic of this kind of control is shown in FIG. 4. Since the rotation speed reduces as the load increases, the problem of file breakage caused in the case of a conventional control wherein the rotation speed is kept constant hardly occurs. In FIG. 4, line a indicates a characteristic (rotation speed) obtained when the duty ratio is raised and the output torque is increased, line c indicates a characteristic obtained when the duty ratio is lowered and the output torque is decreased, and line b indicates a characteristic between the two characteristics. Even when the duty ratio is lowered, the rotation speed at no load is hardly lowered. Therefore, operation can be performed efficiently when the load is small.

In this way, be controlling the output of the motor 2 in accordance with the duty ratio of the pulse voltage, loss due to heat generation at the control circuit is reduced, and the circuit can be made more compact, lightweight and efficient. For these reasons, it is considered that this kind of drive method is particularly suited for cordless apparatuses.

Figure 5:
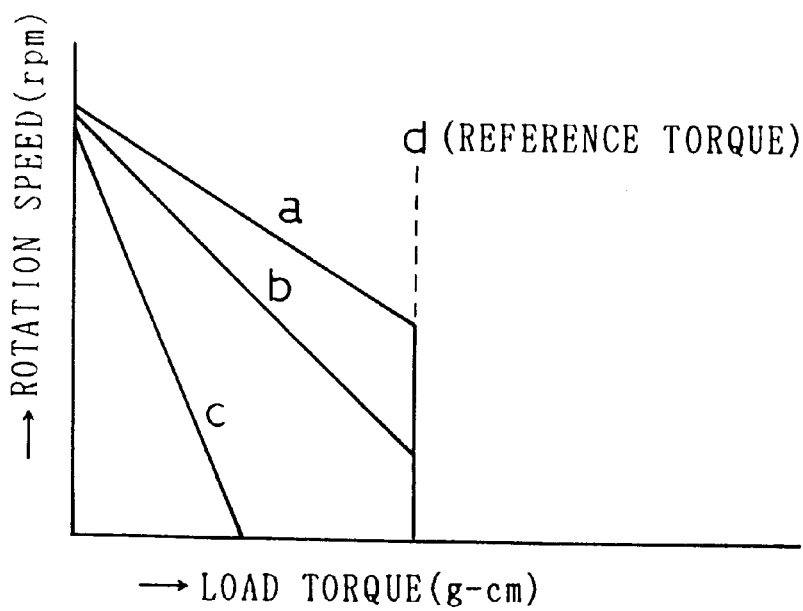
FIG. 5 is another graph showing a motor output characteristic of the controller.

FIG. 5 is a graph showing a characteristic of the motor when the auto-stop control depending on torque is exerted over the conditions shown in FIG. 4. More specifically, line d designates the reference torque. When the CPU 1 detects that the load torque has reached the reference torque d, the control signal from the port 4a is not delivered, the transistor switch 3 is turned off, and the motor 2 stops. The reference torque d can be selected as desired from values in a fixed range by using the variable resistor 11 for setting the reference torque, and the load torque is detected when the voltage generated at the load torque detection resistor 6 owing to the current of the motor 2 is supplied from the port 6a to the CPU 1. The preset reference torque d is indicated at the reference torque display portion 8b.

Accordingly, by properly setting the reference torque d in accordance with the type or the like of the file to be used, the file 17 is securely prevented from breaking owing to excessive loads. When the rotation speed is reduced, the cutting performance of the file is lowered significantly, and cutting is not performed substantially. Therefore, instead of completely stopping the motor 2 when the load torque has reached the reference torque d, it may be possible to reduce the rotation speed by lowering the duty ratio.

Figure 6A:
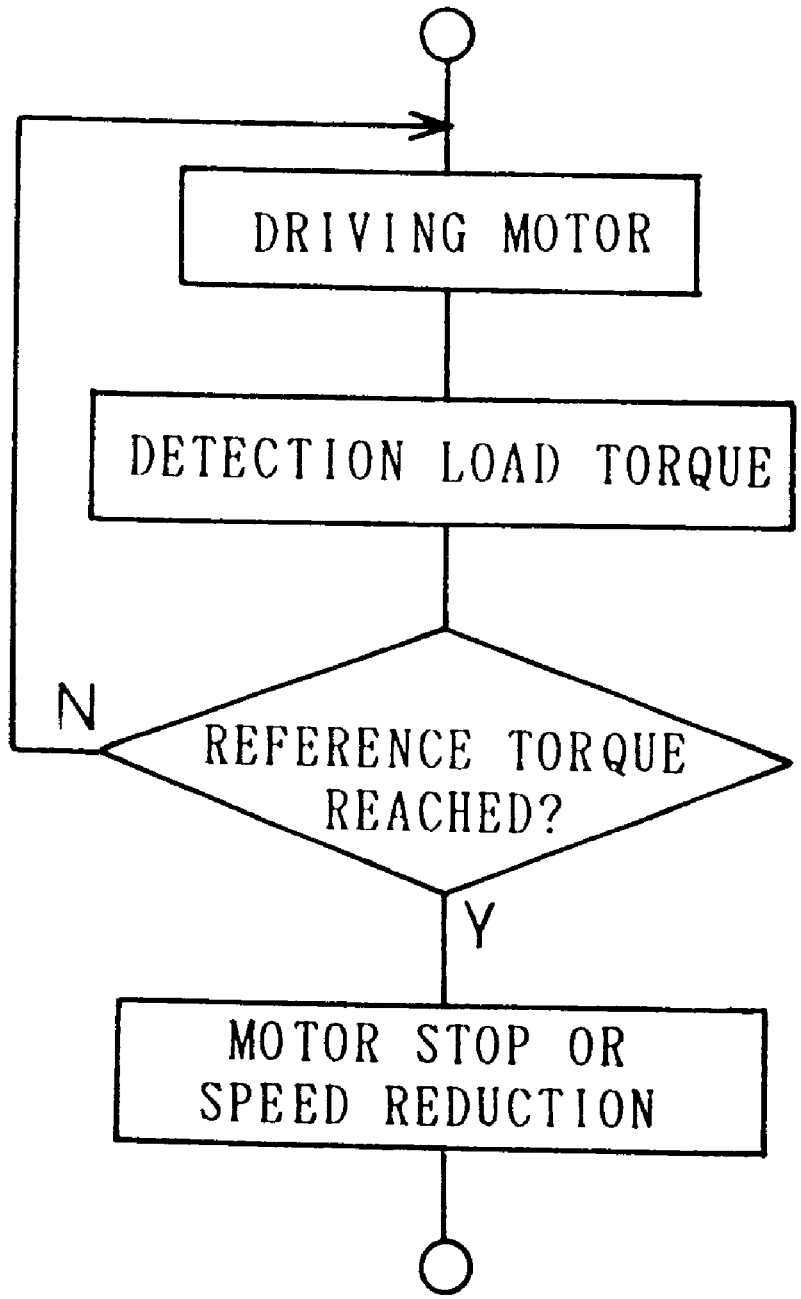
FIG. 6A is a flowchart showing the control procedure for motor stop or rotation speed reduction depending on load torque in the controller.

FIG. 6A is a flowchart showing the procedure for the auto-stop control depending on the torque described above. Stopping the motor or reducing the motor rotation speed when the load torque has reached the reference torque should be determined beforehand and built in a program.

Alternatively, either of the two cases is made selectable by the operator via a selection switch provided additionally.

This control corresponds to claim 2 of the present invention and is effective in preventing file breakage. However, even when cutting is substantially stopped by stopping the motor 2 or by reducing the rotation speed, the file 17 may remain cutting into a root canal. This problem can be solved by auto-reverse control described below.

The auto-reverse control corresponds to claim 3 of the present invention and is exerted so as to temporarily reverse the motor 2 when the load torque has reached the reference torque. By this control, the file 17 having cut into a root canal and having been hard to rotate can be moved back slightly so as to resume an easily rotatable condition. This prevents the file from not only breaking but also from cutting into root canals. This reverse rotation of the motor 2 is performed by shifting the rotation direction selection switch 5 comprising a small relay or the like to the reverse rotation setting side in accordance with a selection signal from the port 5a of the CPU 1. The duration for the reverse rotation is selected in the range of 0.1 to 2 seconds. However, a time of about 0.5 seconds is sufficient in usual cases. In addition, it may be possible to set the reverse rotation speed as necessary.

In this control, it may be possible to temporarily stop operation by stopping the motor 2 after the motor is rotated reversely. However, it is also possible to continuously perform operation by automatically repeating motor operation comprising temporary reverse rotation performed each time the load torque has reached the reference torque d and forward rotation resumed after the reverse rotation. With this method, operation can be performed efficiently. The resumed forward rotation can be started automatically when the above-mentioned reverse rotation duration has passed. However, without setting such a reverse rotation duration, it is possible to adopt a control method wherein the forward rotation is resumed after confirming that the load torque has become lower than the reference torque.

In this case, since the load torque during the reverse rotation is usually less than that during the forward rotation, the load torque becomes lower than the reference torque immediately after the reverse rotation. Reverse and normal rotations are thus repeated frequently, resulting in unstable operation and adversely affecting the service life of the apparatus. Therefore, it is desirable that control with a hysteresis characteristic should be performed so as to start forward rotation when the load torque is not more than a second reference torque which is set at a value slightly lower than the reference torque. The difference between the reference torque and the second reference torque, namely the width of hysteresis, can be set to a fixed value suited for clinical purposes, or can be changed as necessary.

Figure 6B:
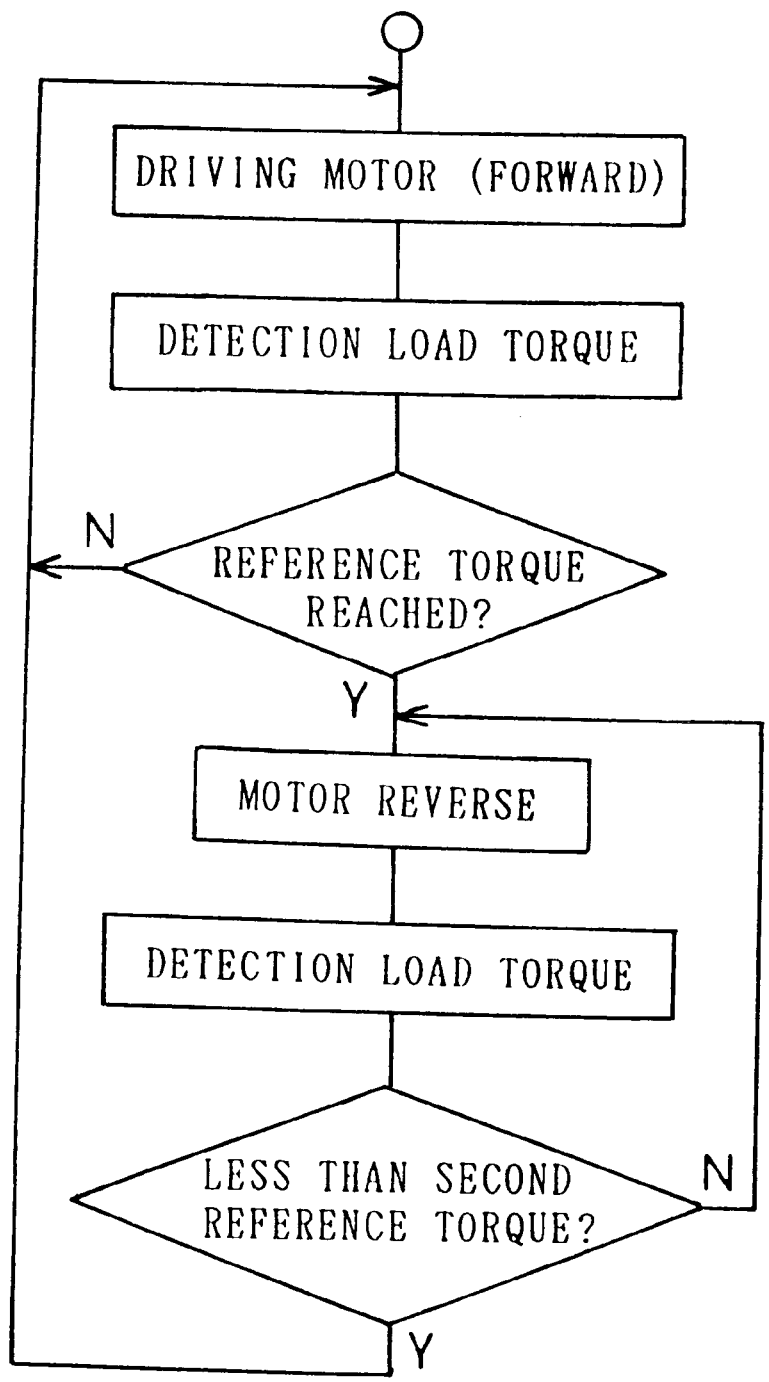
FIG. 6B is a flowchart showing the control procedure for motor reverse rotation depending on load torque in the controller.

FIG. 6B is a flowchart showing the control procedure for performing operation while repeating reverse and forward rotations. The figure shows only the basic procedure. In actual practice, however, the motor 2 is stopped for a short time when reverse rotation is shifted to forward rotation and when forward rotation is shifted to reverse rotation.

As shown in FIG. 1, the handpiece 21 is provided with the root canal length measurement circuit 7 so as to perform auto-stop control depending on tool position in addition to the auto-stop control depending on torque and the auto-reverse control described above. In this auto-stop control depending on tool position, the root canal length measurement circuit 7 detects the position of the tip of the file 17 at all times. When the measurement circuit 7 detects that the tip has reached a reference position, a signal indicating the detection is supplied from the measurement circuit 7 to the port 7a of the CPU 1, and the motor 2 is stopped by the control signal delivered from the port 4a. The reference position can be set as desired in a fixed range by using the variable resistor 13, and the reference position thus determined is indicated at the reference position display portion 8c.

Since the auto-stop control depending on tool position is also intended to stop substantial cutting, it may be possible to reduce the rotation speed by lowering the duty ratio instead of stopping the motor 2 when the tip has reached the reference position. Alternatively, just as in the case of the above-mentioned auto-reverse control, it may be possible to temporarily rotate the motor 2 reversely. Stopping the motor, reducing the rotation speed or reversing the motor should be selected and built in a program. Alternatively, it may be possible for the operator to select one of the methods via a selection switch provided additionally.

Figure 7:
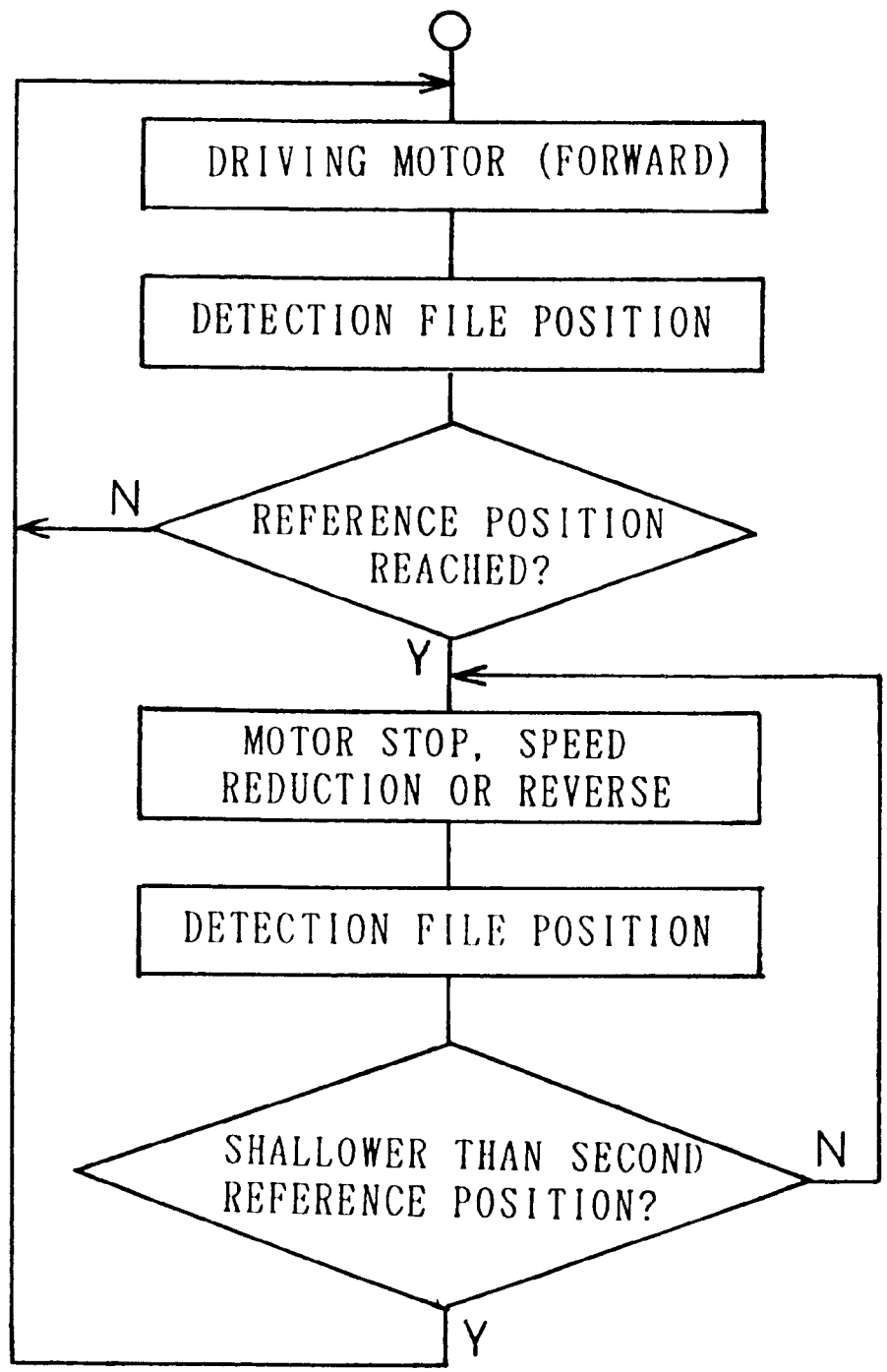
FIG. 7 is a flowchart showing the control procedure for motor stop, rotation speed reduction and reverse rotation depending on tool position in the controller.

FIG. 7 is a flowchart showing the basic control procedure for the auto-stop control depending on tool position. In this procedure, the position of the file is detected after the motor 2 is stopped or reversed once. When the file 17 is extracted slightly and the tip is set at a shallower position by the operator, the forward rotation of the motor 2 is automatically resumed. A hysteresis characteristic is also provided between the stop or reverse rotation and forward rotation. In other words, a second reference position slightly shallower than the reference position is set, and the motor is rotated forward when the position of the cutting tool is shallower than the second reference position. With this procedure, since operation can be performed continuously while the file is inserted and extracted repeatedly, efficient operation is possible. The width of the hysteresis can be set at a proper fixed value, or can be changed as necessary.

As clarified by the above-mentioned explanations, the procedures shown in FIGS. 6A and 6B regarding the auto-reverse control and the procedure shown in FIG. 7 regarding the auto-stop control depending on tool position are performed simultaneously in the embodiment. In other words, these procedures are carried out alternatively in parallel by executing interruptions. When the condition for stopping or reversely the motor 2 has been established, the operation corresponding to the established condition takes priority and is performed. Because of the combination of these procedures, the file is prevented from breaking and cutting into root canals by the auto-reverse control, and penetrating root apexes is also prevented by the auto-stop control depending on tool position. Therefore, by applying the present invention to motor control at the time of root canal formation for example, the operability of the root canal treatment apparatus can be improved significantly, whereby the apparatus can be made highly practical.

Figure 8:
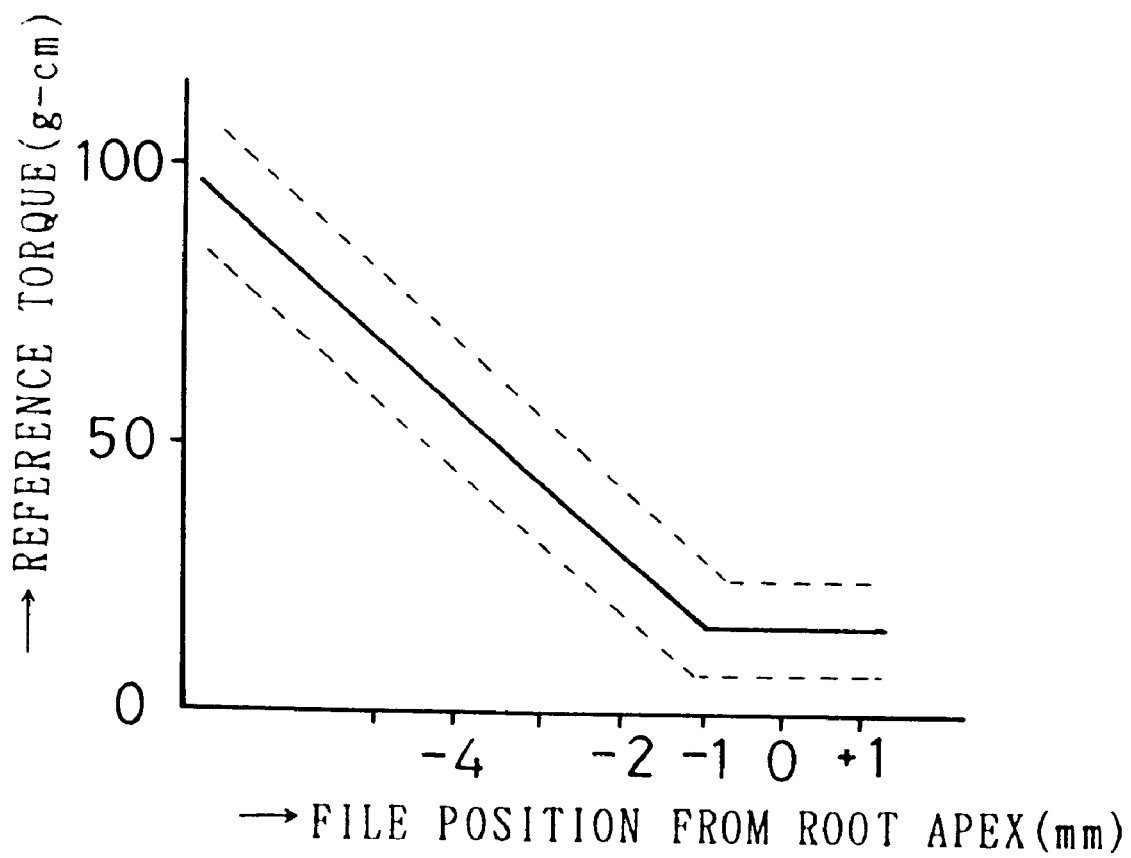
FIG. 8 is a graph showing the relationship between the file position from a root apex and the reference torque in the controller.

As the tip of the file 17 comes closer to a root apex, the file 17 is apt to break while it is secured. It is thus desirable that the reference torque for the auto-reverse control should be smaller as the tip comes closer to the root apex. Therefore, when the root canal length measurement function is also used just as in the above-mentioned example, the tip position of the file is detected successively. The reference torque can thus be changed automatically by the control through the CPU 1. FIG. 8 is a graph showing an example of the control. The reference torque is kept at the minimum fixed value in the vicinity of a root apex, and becomes larger as the position of the file is away from the root apex. The level of the characteristic curve is adjusted by the variable resistor 11 for setting the reference torque within a fixed range as indicated by broken lines.

In addition to the normal appropriate rotation speed for usual cutting, the rotation speed immediately before the load torque or tool position has reached the reference value, or a speed lower the rotation speed can also be used as the motor rotation speed at the time of resuming cutting in the above-mentioned control examples. One of these speeds should be selected beforehand and built in a program. Alternatively, it may be possible for the operator to select one of the speeds as desired via a selection switch.

When the auto-reverse control is performed during operation using a file, a force pushing out the file toward a root canal orifice is generated during the reverse rotation of the motor, and a force raising the head is generated at the handpiece. As a result, the head is moved up and down by the repeated forward and reverse rotations. The operator can thus bodily senses the cutting conditions. As a result, the apparatus offers a nice feel and is easy to use.

In the above-mentioned explanations, it is assumed that the cutting tool, namely the file 17, is rotated continuously in one direction by the motor 2. However, as the action of the cutting tool such as the file, instead of the continuous rotation, it is possible to use a twist drive method wherein forward and reverse rotations are repeated in a fixed range, or a drive method wherein the cutting tool is vibrated in its axial direction. When these drive methods are adopted, it is meaningless to use the reverse rotation control of the motor. However, since the auto-stop function activated by motor stop or rotation speed reduction can be performed without hindrance, the present invention is applicable as it is to such methods.

It may be possible to provide an on/off switch for each of the auto-stop control depending on torque, the auto-reverse control and the auto-stop control depending on tool position so that each function can be turned on and off selectively as necessary.

Although the display device 8 comprising LEDs is shown in FIG. 2B, a display devices employing other light-emitting elements can also be used, or a notification device generating sound, such as buzzer sound, or synthesized voice can also be used. As such a notification device, a method of generating notification sound when the load torque has reached the reference torque or when the tool has reached the reference position can be used. Furthermore, many other methods can also be used. For example, pulse sound is generated at all times, and the torque and position are notified successively in accordance with the period of the pulse sound. When the reference torque or reference position has been reached, the state is notified in shorter specific periods. This kind of notification via sound or voice is convenient, since the operator can confirm the load torque or tool position without turning his or her eyes to the notification device.

In FIG. 1, the variable resistors 11, 12 and 13 are provided to set the reference torque, duty ratio and reference position, respectively. However, this is taken just as an example. Instead of the continuous adjustment method using the variable resistors, other methods can also be used. For example, a plurality of switches can be used for step-by-step selection.

What is claimed is:

1. A dental handpiece for forming root canals comprising a cutting tool for forming root canals, a drive motor for driving said cutting tool, a torque detection means for detecting a load torque applied to said cutting tool, and a control means for automatically stopping said drive motor, stopping said drive motor for a short time after reducing a rotation speed of said drive motor, and reversing said drive motor when a detected load torque has reached a preset reference torque, and a reference torque setting means for setting said preset reference torque.

2. A dental handpiece for forming root canals comprising a cutting tool for forming root canals, a drive motor for driving said cutting tool, a torque detection means for detecting a load torque applied to said cutting tool, a position detection means for detecting a position of said cutting tool also used as a root canal length measurement electrode, a control means for automatically stopping said drive motor or stopping for a short time said drive motor after reducing the speed of said drive motor and reversing rotation of said drive motor when a detected load torque has reached a preset reference torque or when said cutting tool has reached a preset reference position, a reference torque setting means for setting said preset reference torque, and a reference position setting means for setting said preset reference position.

3. A dental handpiece for forming root canals according to claim 2, wherein said control means repeats a temporary reverse rotation and forward rotation of said drive motor each time said detected load torque has reached said preset reference torque or each time said cutting tool has reached said preset reference position.

4. A dental handpiece for forming root canals according to claim 1, 2 or 3, further comprising a display means for displaying said preset reference torque set by said reference torque setting means.

5. A dental handpiece for forming root canals according to claim 4, wherein said reference torque setting means and said reference torque display means are provided on a main body of said dental handpiece.

6. A dental handpiece for forming root canals according to claim 2 or 3, wherein said control means rotates said drive motor forward again when said detected load torque has become lower than said reference torque after having reached said reference torque or when a detected position of said cutting tool has become shallower than said reference position after having reached said reference position.

7. A dental handpiece for forming root canals according to claim 6, wherein after said drive motor is rotated reversely, said control means rotates said drive motor forward when said load torque has become lower than a second reference torque which is small than said reference torque, or when a position of said cutting tool has become shallower than a second reference position which is shallower than said reference position.

8. A dental handpiece for forming root canals according to claim 6, further comprising a notification means for notifying via sound or voice a load torque detected by said torque detection means or a position of said cutting tool detected by said position detection means.

9. A dental handpiece for forming root canals according to claim 6, further comprising a display means for displaying said preset reference torque set by said reference torque setting means.

10. A dental handpiece for forming root canals according to claim 9, wherein said reference torque setting means and said reference torque display means are provided on a main body of said dental handpiece.

11. A dental handpiece for forming root canals according to claim 6, further comprising a display means for displaying said preset reference position set by said reference position setting means.

12. A dental handpiece for forming root canals according to claim 6, wherein any of said reference torque setting means, said reference position setting means, a reference torque display means for displaying said preset reference torque set by said reference torque setting means, and a reference position display means for displaying said preset reference position set by said reference position setting means are provided on a main body of said handpiece.

13. A dental handpiece for forming root canals according to claim 2 or 3, further comprising a notification means for notifying via sound or voice a load torque detected by said torque detection means or a position of said cutting tool detected by said position detecting means.

14. A dental handpiece for forming root canals according to claim 13, further comprising a display means for displaying said preset reference torque set by said reference torque setting means.

15. A dental handpiece for forming root canals according to claim 14, wherein said reference torque setting means and said reference torque display means are provided on a main body of said dental handpiece.

16. A dental handpiece for forming root canals according to claim 13, further comprising a display means for displaying said preset reference position set by said reference position setting means.

17. A dental handpiece for forming root canals according to claim 13, wherein any of said reference torque setting means, said reference position setting means, a reference torque display means for displaying said preset reference torque set by said reference torque setting means, and a reference position display means for displaying said preset reference position set by said reference position setting means are provided on a main body of said handpiece.

18. A dental handpiece for forming root canals according to claim 2 or 3, further comprising a display means for displaying said preset reference position set by said reference position setting means.

19. A dental handpiece for forming root canals according to claim 2 or 3, wherein any of said reference torque setting means, said reference position setting means, a reference torque display means for displaying said preset reference torque set by said reference torque setting means, and a reference position display means for displaying said preset reference position set by said reference position setting means are provided on a main body of said handpiece.

20. A dental handpiece for forming root canals comprising::
   a cutting tool for forming root canals;
   a drive motor for driving said cutting tool;
   a position detection means which uses said cutting tool as an electrode that measures a length of said root canals, said position detection means further detecting a position of said cutting tool;
   a control means for automatically stopping said drive motor or stopping said drive motor for a short time after reducing the speed of said drive motor and reversing the rotation of said drive motor when said cutting tool has reached a preset reference position; and
   a reference position setting means for setting said preset reference position.

21. A dental handpiece according to claim 20, wherein said control means repeats a temporary reverse rotation and forward rotation of said drive motor each time said cutting tool has reached said preset reference position.

22. A dental handpiece according to claim 21, wherein said control means rotates said drive motor forward again when a detected position of said cutting tool has become shallower than said reference position after having reached said reference position.

23. A dental handpiece according to claim 22, wherein after said drive motor is rotated reversely, said control means rotates said drive motor forward when a position of said cutting tool has become shallower than a second reference position which is shallower than said reference position.

24. A dental handpiece according to claim 20 or 21, further comprising a notification means for notifying via sound or voice a position of said cutting tool detected by said position detection means.

25. A dental handpiece according to claim 20, 21 or 22, further comprising a display means for displaying said preset reference position which is set by said reference position setting means.

26. A dental handpiece for forming root canals according to claim 25, wherein said reference position setting means and said reference position display means are provided on a main body of said handpiece.

* * * * *